(12) United States Patent
Wedemeyer

(10) Patent No.: US 9,567,847 B2
(45) Date of Patent: Feb. 14, 2017

(54) METHOD OF DATA VOLUME REDUCTION FOR TRANSMISSION ON A LIMITED COMMUNICATIONS CHANNEL

(71) Applicant: Hannes Wedemeyer, Tomball, TX (US)

(72) Inventor: Hannes Wedemeyer, Tomball, TX (US)

( * ) Notice: Subject to any disclaimer, the term of this patent is extended or adjusted under 35 U.S.C. 154(b) by 559 days.

(21) Appl. No.: 14/465,088

(22) Filed: Aug. 21, 2014

(65) Prior Publication Data
US 2015/0091738 A1    Apr. 2, 2015

Related U.S. Application Data

(60) Provisional application No. 61/885,919, filed on Oct. 2, 2013.

(51) Int. Cl.
| | |
|---|---|
| E21B 47/06 | (2012.01) |
| E21B 47/09 | (2012.01) |
| H04W 4/02 | (2009.01) |
| G01N 29/11 | (2006.01) |
| A61B 5/0452 | (2006.01) |
| G01V 1/34 | (2006.01) |
| H04L 29/06 | (2006.01) |
| F16L 101/30 | (2006.01) |

(52) U.S. Cl.
CPC ............ *E21B 47/09* (2013.01); *H04W 4/02* (2013.01); *A61B 5/0452* (2013.01); *F16L 2101/30* (2013.01); *G01N 29/11* (2013.01); *G01V 1/34* (2013.01); *H04L 69/04* (2013.01)

(58) Field of Classification Search
CPC ....... E21B 47/09; F16L 2101/30; H04L 69/04; H04W 4/02; A61B 5/0452; G01V 1/34; G01N 29/11
See application file for complete search history.

(56) References Cited

U.S. PATENT DOCUMENTS

| | | | |
|---|---|---|---|
| 6,791,311 B2* | 9/2004 | Murphy | G01R 29/0842 324/72 |
| 8,825,148 B2* | 9/2014 | Zhang | A61B 5/0456 600/523 |
| 8,831,886 B2* | 9/2014 | Williams | G01V 1/50 166/250.01 |
| 8,868,168 B2* | 10/2014 | Zhang | A61B 5/0452 600/516 |
| 2004/0261547 A1* | 12/2004 | Russell | F17D 5/00 73/865.8 |
| 2006/0143335 A1* | 6/2006 | Ramamoorthy | G09G 5/006 710/58 |
| 2008/0215257 A1* | 9/2008 | Stripf | G01N 29/07 702/38 |

(Continued)

*Primary Examiner* — Mohamed Barakat
(74) *Attorney, Agent, or Firm* — The Law Offices of Kevin M. Jones & Associates, LLC

(57) ABSTRACT

A method of recording and classifying data collected from an above ground marker for pipeline pig monitoring. Described herein is a method of extracting minimum data attributes from a real-time data sample and packaging same to achieve a significant volume reduction such that the information can be conveyed across communications channels with limited bandwidth. The reduced volume of information can then be utilized at a remote location to reconstruct a close approximation of the original signal with precise timing, and sufficient clarity to allow remote operators to identify pertinent information from the original data sample.

18 Claims, 7 Drawing Sheets

(56) References Cited

U.S. PATENT DOCUMENTS

2009/0292475 A1* 11/2009 Alam ..................... G01V 1/34
                                                    702/14
2013/0073263 A1*  3/2013 Sieracki ................ G10L 25/00
                                                    702/190

* cited by examiner

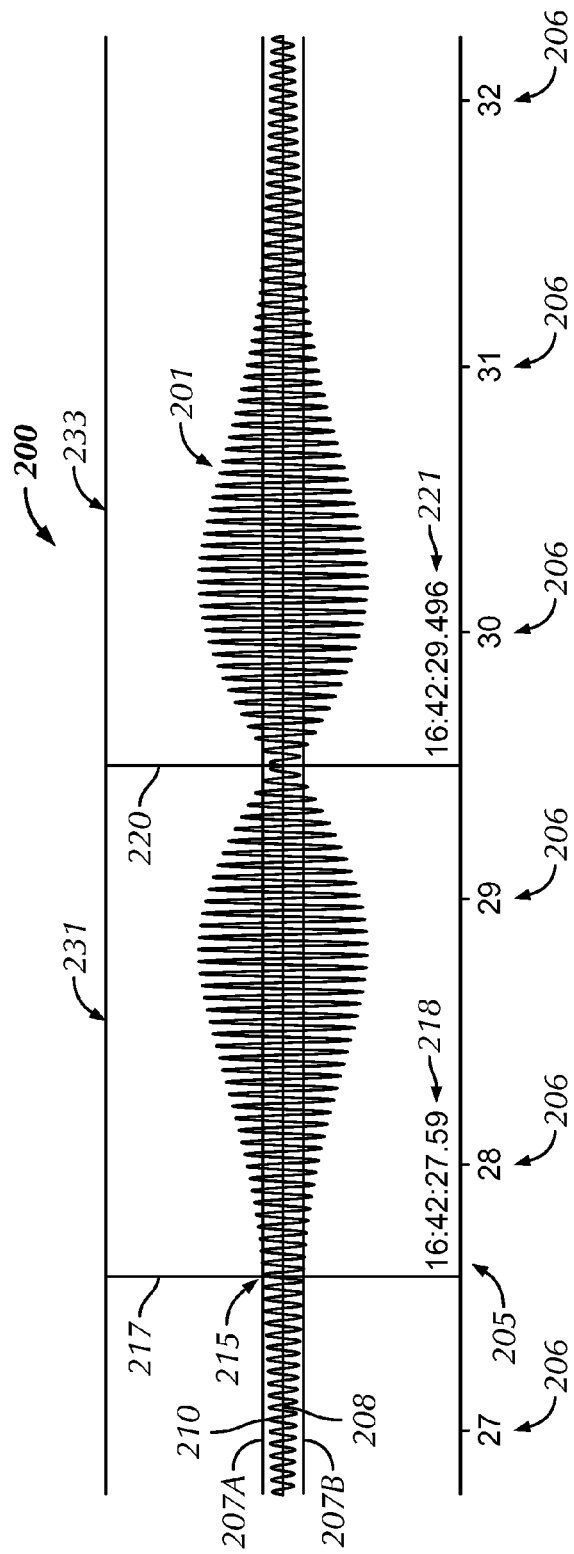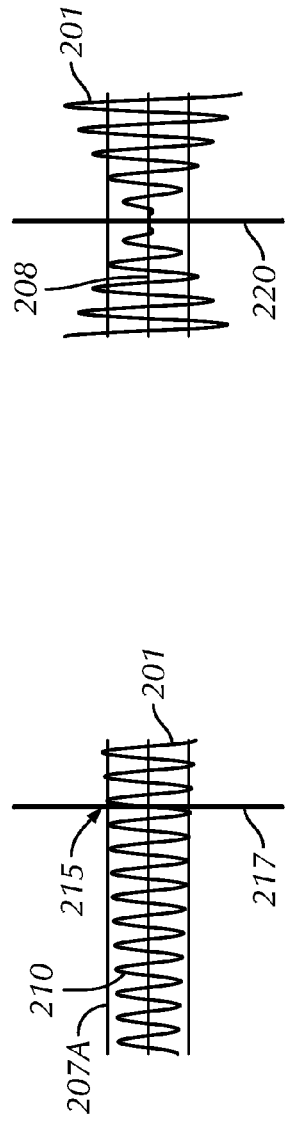

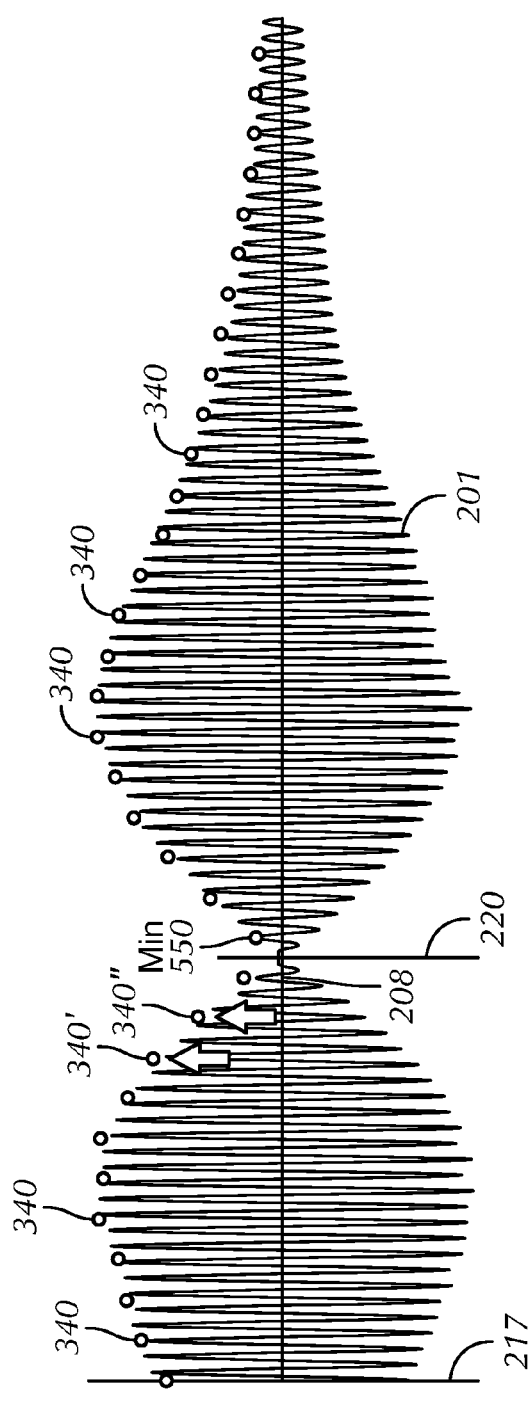
FIG. 5
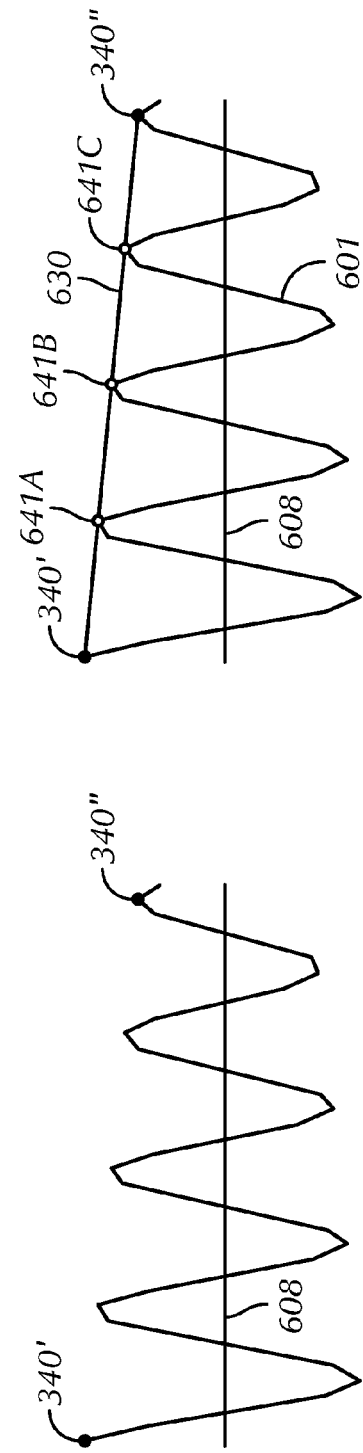
FIG. 6A
FIG. 6B

METHOD OF DATA VOLUME REDUCTION FOR TRANSMISSION ON A LIMITED COMMUNICATIONS CHANNEL

CROSS-REFERENCE TO RELATED APPLICATIONS

This application claims priority under 35 U.S.C. §119(e) from U.S. Provisional Patent Application No. 61/885,919, by Hannes Wedemeyer, "Method of Data Volume Reduction for Transmission on a Limited Communications Channel" filed the 2 Oct. 2013, which, by this statement, is incorporated herein by reference for all purposes.

NOTICE OF INTENT TO RESERVE COPYRIGHT OR MAST WORK RIGHTS

A portion of the disclosure of this patent document contains material which is subject to copyright protection. The copyright owner has no objection to the facsimile reproduction by any one of the patent documents or the patent disclosure, as it appears in the Patent and Trademark Office patent file or records, but otherwise reserves all copyright rights whatsoever.

BACKGROUND OF THE INVENTION

Knowledge of the path and progress of instrumented pipeline-inspection tools ("pigs") flowing with product through pipelines is highly desired, especially if the pig becomes stuck in the pipeline. It is common for a pig to carry a portable transmitter or magnets which allow its passage to be detected by instruments placed in the Right of Way on the ground surface above the pipeline. These tools are referred to herein as Above Ground Markers (AGMs). Pigs with portable transmitters may emit a continuous signal, or may emit a pulsed signal. One skilled in the art would appreciate that other variations may also occur in the transmitter signal which can be accounted for in the detection of the pigs to distinguish the transmission from noise, and improve identification.

The type of transmitter carried by a pig is determined by the purpose of the pig. When timing accuracy is important a continuous transmitter is desired, as it allows for a clearer null signal as the transmitter passes under an AGM. Similarly magnetic signals can be utilized for precise timing as they generate a clear zero crossing as the pig passes under the AGM. Precise timing is necessary to correlate the data collected by the pig's instruments with known time stamps and geographic locations. Therefore, drifts and other "dead reckoning" errors from the pig's onboard inertial navigation instruments can be adjusted to precisely determine the location of 'defect' conditions recorded by the pig.

Pulsed signals may be more desirable for instances where precise timing is not required, such as cleaning pigs. Cleaning pigs do not normally collect and record data in the pipeline, so the reason for tracking them is to ensure they are properly progressing through the system, and identify their specific location if they get stuck. Since it may take time to locate a stuck pig, the pulsed signals are desirable as they give longer running times than continuous transmitters given a specific amount of battery life. E.g., A pulsed signal pig with a 50:50 duty cycle is expected to operate for approximately twice as long as a continuous signal pig with the same battery life.

AGMs detect and report electronic signals from the pig as it passes through the pipeline. As the pig is passing through a pipe, the pipe's construction may shield its transmission signal. The pipe may also be buried under more than twenty feet (20') of ground. This attenuation of the transmission signal means the AGM must be very sensitive. This sensitivity results in many false signals being detected which may be mistaken for the signal of the passing pig.

Typically, human operators must be on numerous sites along the pipeline to monitor these instruments and report the pig's progress (or lack thereof). This process of monitoring the pig so that its location can be approximated in the case it becomes stuck involves significant expense.

Some instrument packages exist that contain additional electronics which allow automatic unattended recording of the detected signals and thus the efficient transmission of these results to remote observers is desirable. However, due to the remote locations of most pipelines, transmission must be accomplished by satellite links which can be an expensive transmission medium.

The most cost-effective satellite links allow only a very limited amount of data per transmission, usually single packets of less than sixty (60) bytes, and rarely more than a few hundred bytes. For this reason, it has been a common practice to transmit a standard identification message when the pig passage event has occurred. No actual data of the event is transmitted by these systems. Rather, they rely purely on the time stamp applied to a message when the satellite ground server receives and forwards the standard message. This data packet is transmitted three times in approximately seven and a half minute increments to account for gaps in satellite coverage which may prevent a single data transmission from being received. The data is relayed by a satellite to a ground station where the message is forwarded by other communications means to a final destination. A common means of forwarding the data is via the Internet in the form of e-mail or Short Message Service (SMS) Text Messages.

Depending on which of the three transmitted data packets was received and forwarded, the server time stamp may differ from the actual pig passage time by as much as fifteen (15) minutes. When a pig is being utilized to determine flow rates, this delay can result in a significant error in calculations. Environmental conditions are often detected by the AGMs, and can trigger the AGM in the same manner as a passing pig. Transmitting a signal each time a triggering event occurs without any further information can result in false transmissions causing remote monitors to believe a pig has passed when such an event has, in fact, not occurred.

The current method of remote monitoring is to estimate when a pig passage is anticipated, and watch for a signal to arrive approximately at the anticipated time. If a signal is received, then the remote monitor assumes it was the signal of the pig passage. If more than one is received, then the one closest to the estimated arrival time is assumed to be the correct signal and the others are rejected as false signals. These assumptions result in a lot of unreliable "guess" work which is costly to the industry.

BRIEF DESCRIPTION OF THE DRAWINGS

FIG. 2 illustrates an exemplary data sample as seen by an AGM in the field.

FIG. 2A illustrates an enlarged portion of FIG. 2 illustrating the signal at the point in which data collection begins.

FIG. 2B illustrates an enlarged portion of FIG. 2 illustrating the signal at the point in which the pig transverses the immediate detector area.

FIG. 5 illustrates how the reduced data corresponds to and represents the original data.

FIGS. 6A and 6B illustrate a method of utilizing the reduced data to reconstruct the original data at a remote location in accordance with an exemplary embodiment of the invention.

DETAILED DESCRIPTION OF THE PREFERRED EMBODIMENTS

Figure 1:
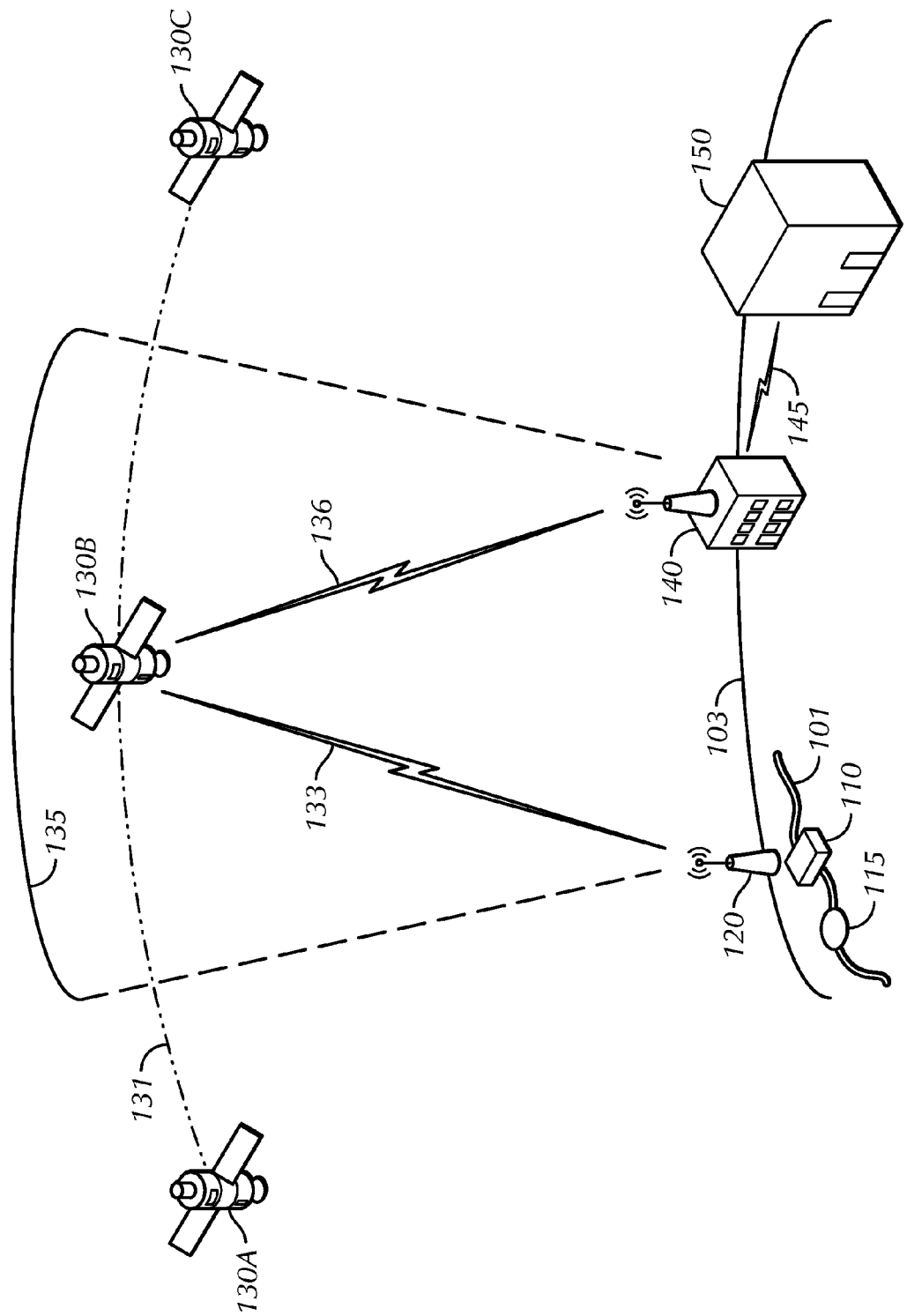
FIG. 1 illustrates a standard environment in which the innovation is utilized in accordance with an exemplary embodiment of the invention.

A more comprehensive reporting method would contain both details of the original signal and a precise time stamp of when the event occurred, rather than a timestamp by the satellite server corresponding to when a message regarding the event was finally delivered. The ability to evaluate the detection signal as received on site is vital to pig tracking By extracting the minimum data attributes necessary to convey the pertinent characteristics of the raw data, communications through limited communications channels is possible to allow pseudo reconstruction of the shape of the original signal but with precise timing data at a remote location.

Signal interpretation is sometimes difficult due to the many varying and unpredictable physical conditions in or near the pipeline which may cause a false trigger of the detecting mechanisms. The customer's ability to view the actual signal produced by the pig detector can greatly increase the reliability of the final interpretation of the recorded event.

Adding the Global Positioning System (GPS) position of the pig detector device into the message data is clearly helpful in documenting the reported event. Timing accuracy is especially important when pig passage time is used to estimate pipeline product flow rate or in predicting its arrival at any given location.

In rare cases, the pig detector instrument originating the raw data becomes missing, lost, or stolen in the sometimes long interval it remains on the Pipeline's Right of Way before retrieval. In this case, the valuable timing information used for correcting onboard inertial navigation instruments in an instrumented pig is saved by using the passage time and location sent immediately to the customer. That is, utilizing the methods described herein, sufficient resolution of pertinent data is conveyed from an AGM to a remote receiver such that the conveyed data can be considered a "back up" if an AGM becomes lost or damaged. The reconstruction from the "back up" transmitted data may substitute for actual data if an AGM is not recovered from the field with its actual data intact. The reconstructed data is sufficiently reliable that post processing of a pig's inertial navigation data may utilize the reconstructed data without inducing errors to surrounding areas of the pig's continuous data stream from the inertial navigation systems, or in locating defects by time correlation with the inspection tools recorded data.

The present innovation comprises a procedure to process the raw data into a series of time based sampling of the amplitude of a narrowband signal. The data can then be transmitted and reconstructed at a remote monitoring location such that a reliable determination can be made between false triggers and desired signals.

The AGM monitors incoming signals. When a signal exceeds a threshold, the AGM begins recording the signal and marks a known point of the signal with the current time corresponding to when the signal was received. The recording continues through an approach period where it is assumed the pig is approaching the AGM. This is normally characterized in the signal with a rise in amplitude as the unit comes closer to the AGM and a relatively sharp fall in amplitude as the pig passes the zone immediately below the AGM. The signal should "null out," that is, amplitude should briefly go to approximately zero after which the pig is retreating. During the retreat, the amplitude sharply rises to a maximum before beginning a dissent back down to the level of ambient signal noise.

This characteristic curve is seen in magnetic detection as well, but without the multi-hertz carrier wave. Additionally, a pulsed signal, ignoring the predicted interruptions caused by the pulsing, displays the same overall low frequency curve. The ultimate shape of the signal may be affected by pipeline construction, depth, etc. A pipeline made of metals will attenuate a signal more than a plastic pipeline. Thicker wall pipe will attenuate signals more than a thin walled pipe. Additionally, pipe sleeves or conduit can have the same effects of attenuating signals. A deeper pipeline will yield a weaker signal than a shallow or surface pipeline.

Minor glitches may be caused by pipe joints debris near the detector, passing vehicles, etc. For this reason it is most desirable to transmit the signal to the remote monitor for reliable interpretation and analysis. For instance, a plastic pipe or thin walled steel pipe may result in a saturated signal at the detector, where a metal pipe may have shielded a large portion of the signal. Iron deposits in the soil disturbed by pipeline construction may result in minor attenuations in the signal which can confuse detection.

The preferred method of recording is to sample the incoming signal at fixed sampling intervals and store the raw data samples. Proper frequencies for sampling intervals to prevent signal aliasing are well understood by those skilled in the art and therefore are not discussed further here. A properly sampled signal results in far too much data to efficiently transmit via low-cost, low-bandwith data packet communication systems; therefore, we need to reduce the data volume.

Since the time of the pig passing may be anywhere from a couple of seconds to several minutes, the best signal reconstruction can be achieved by recording as much of the raw data as the AGM can handle, then determining the specific data processing based on the data acquired.

Since we know a "Good" signal will rise and fall during the approach period to a null point in the case of an ELF (Extremely Low Frequency) signal, and a zero crossing point in the case of a magnetic signal, then rise and fall again during the retreat period, we can watch for the fall then anticipate the rise to determine the time period of the approach period.

The total data window period can then be some multiple of this time period. In the preferred embodiment, an approximate factor of two and one half (2.5) of the approach period is utilized as the total sampling period. This results in a sufficient recording of the pig's retreat to allow remote monitors to confidently identify that the signal was a "Good" pig pass signal.

Once the data has been collected, and the data window has been established, the window can be "sliced" into a relatively small number of intervals (S). An amplitude for the signal is established for each interval. This establishes an array of values corresponding to the amplitude of the signal at each interval S along the signal. This array can be transmitted as part of the data packet. The number of slices determines the resolution of the data recreation. Increasing the value of S results in higher resolution, but also results in larger data packets. In the preferred embodiment, the value of S is pre-determined to accommodate a specific data packet size offering the most economical communication options for a given transmitter. In one embodiment, the value of S may be determined based on the size of the data window, or on the volatility of the data sampled.

One method of establishing the array is to traverse the signal samples in the data window, and identify local peak values for the signal, ignoring all other values. From the peak values, select S evenly spaced values, with one of the values corresponding to a known fixed point in time.

To obtain a higher resolution, the signal may be rectified prior to processing. This results in a doubling of the number of positive half cycles of the carrier wave, which correspondingly results in double the peak values from which to select the S evenly spaced values. One skilled in the arts would appreciate that since the signal is reflected above and below the zero line, the same operations would apply to the negative half cycles as well. For simplicity, this application will focus only on the positive side of the signal.

The preferred method of processing the sampled signal is to rectify the values, then detect the peak of each half-cycle and build an array of these peak values (referred to hereinafter as the Peak Array.) The Peak Array has one value for each half cycle in the data sample of the data window.

Traversing the original data, a peak is identified by comparing each value to the previous value to determine if the current value is higher than the previous. If the current value is higher than the previous, then it becomes the new peak value. This peak value is stored in the array for each subsequent data location, until the next peak is located. The resulting array is a list of repetitive peak values for the duration of each cycle of the ELF carrier wave.

Dividing the number of samples in the raw data array, N, by the number of desired amplitude slices, S, gives us the number, X, of raw data samples per amplitude slice. Starting from the first recorded value in the raw data array, we take each $X^{th}$ value to build an array of amplitude slice data (referred hereinafter as the Amplitude Slice Array.) The first value in the Amplitude Slice Array corresponds to the trigger of the signal, which has a recorded timestamp associated with it, (referred to hereinafter as the Left Window Time.) The Amplitude Slice Array can be utilized along with the value of X and the Left Window Time to recreate the original data with sufficient precision to allow reliable use in post inspection run processing.

The AGM should include a reliable time stamp capability. One skilled in the art would appreciate that GPS activities also require reliable time tracking; therefore it would seem obvious to utilize the timestamp of the GPS components. However, it is common practice to place AGMs in locations where a GPS signal may not be received reliably. In one such situation, AGMs are buried so they are not seen by the casual observer. A buried unit would not be able to communicate with GPS, but could update its internal precision clock from a GPS signal prior to burying, then maintain a relatively reliable timestamp after burying.

The Left Window Time is used as the starting time for the reconstructed signal at the remote receiver. Given the Left Window Time, the number of samples per amplitude slice (X), and the Amplitude Slice Array, the signal can be reproduced. The number of raw data samples per amplitude slice (X), is inversely proportional to the number of slices (S) for a given data window length. The number of amplitude slices can be increased to improve resolution; however, increasing S results in more data transmitted across the communications medium.

An alternative method involves decreasing the resolution of the amplitude for each slice to allow additional slices to be taken for a given byte size. If the amplitude is transmitted in 8-bit format, then 42 values would take 336 bits of data. Using amplitudes with 7-bit format allows 48 values to be transmitted utilizing the same 336 bits of data. Utilizing a 6-bit format for amplitude results in 56 values in the 336 bits.

In the preferred embodiment, the transmitted data packet includes at least:
AGM identifier
Left Window Time
Latitude and Longitude of the AGM's Location
Type of Signal (ELF or Magnetic)
Frequency of the Carrier (if an ELF signal)
Number of Raw Data Points between the Sample Amplitudes (X)
Amplitude Slice Array (an array of S values)

One skilled in the art would appreciate that the information above may be encoded in numerous formats and still be within the scope of the innovation described herein. Further, one or more of the elements may be combined. As an example, the Frequency of the Carrier may be transmitted as zero to indicate that the signal type is magnetic, or the Frequency may be transmitted as a negative number to indicate that the ELF signal is pulsed.

Additionally, elements may be omitted in some embodiments. As an example, the Latitude and Longitude of the AGM's Location may be omitted and instead logged during placement of the AGM in the field and assumed to remain fixed until confirmed by retrieval of the AGM. In another embodiment, the Left Window Time may be omitted in favor of a repetitive transmission at fixed time increments.

The original signal can be reconstructed by beginning with an oscillation at the ELF frequency with the first amplitude. The ELF frequency is constant through the signal. Subsequent amplitudes can be interpolated successively until the entire signal has been reconstructed into a close approximation to the original signal recorded by the field detector instruments, i.e. the AGM.

An alternative embodiment for reconstruction involves initializing an array of X times S values with the amplitudes from the data packet starting at the initial array position, and loading each successive value into the array at the next $X^{th}$ location. The intermediate values are then calculated by mathematical curve fitting. This array is the Reconstructed Peak Array.

The simplest method of interpolating the intermediate values for the amplitudes is a linear or first degree polynomial curve (i.e. a straight line). This is calculated by determining the slope of a line between the known values, and then proportionately determining the intermediate values.

One skilled in the arts would appreciate that typical sample data smoothly transitions between slice values, and so better approximation can be achieved by utilizing three or more consecutive values from the Amplitude Slice Array to determine a second degree polynomial curve rather than a linear function which may more accurately approximate the intermediate values.

As the frequency of the signal is known, and the initial signal time (Left Window Time) is known, the exact time of any location on the reconstructed signal can be determined with precision. Although the reconstruction is not guaranteed to have a particular sample as a null value corresponding to the raw data's signal null (for ELF signals), or the zero crossing (for magnetic signals) at the specific pig passing, it yields a close approximation that allows the operator to determine a minimal signal on the reconstruction which should correspond to the null or magnetic zero crossing detected by the AGM. This approximation is very accurate since the signal is symmetrical across this region for small time durations. It is also interesting to note that the raw data signal may not have an actual null for ELF signals if the detector is not properly positioned directly over the pipeline.

While the preferred embodiment utilized the Left Window Time as the known time point in the signal, one skilled in the arts would appreciate that the message can include the Coordinated Universal Time (UTC) time or GPS time of any point in the data, which can be used to determine the time of all other points in the data and thus be used to determine the arrival time of a pipeline pig at the pig detector's GPS location. For greatest precision, the UTC or GPS time should precisely correspond with one of the S values in the Amplitude Slice Array. That one point being the starting point, and all timeline data being computed as a difference from that point, determined by the frequency and the number of raw data samples between each amplitude slice, X.

For low frequency signals, such as the field from a steady magnet source on a pig passing the pig detector, the raw signal itself can be handled in the same way as the amplitude of the oscillating ELF signal. For pulsing transmitters, the methods described herein would also work to accurately reproduce a detected signal remotely; however, the pulsing of the transmitter may make it difficult to determine the exact zero crossing if a pulsed-off sequence aligns with the null signal. Raw data viewed at the detection site would suffer the same issue.

In a different embodiment, a data detection device can be manually monitored. A time frame of interest in the data is selected creating a "data window." This data window may be selected and sized irrespective of triggering thresholds or approach time periods and retreat time periods. The specific timestamp of the data window start time is determined from known times of specific data points in the sample. Once the "Left Window Time" is determined, processing of the data proceeds as previously described to reduce the volume of data by generating a representative data packet. This data packet may then be transmitted via limited communications channels on command.

In another embodiment, a unit may be configured to sample continuously, and divide the data into predetermined discrete windows which are then compressed by the previously described methods, thus allowing larger volumes of data to be preserved on smaller storage mediums.

In another embodiment, a unit may be configured to continuously record data and threshold triggers, or other triggering events may be utilized to index events of interest in an otherwise unwieldy data stream. In another embodiment, a unit may be configured to continuously record data in a circular RAM buffer, with events triggering a dump of segments of interest to memory in compressed or uncompressed format.

BRIEF DESCRIPTION OF THE DRAWINGS

FIG. 1 is a schematic drawing of the essential components in a system. A pipeline (101) carrying a pig (115) is monitored by a detector (110) such as an Above Ground Marker, which utilizes a satellite transmitter (120) to communicate (133) with orbiting satellites (130). The orbiting satellites (130) relay (136) the information to a receiving station (140) which then forwards the communication (145) to remote receivers (150).

Due to the spacing of the satellites (130A-C) in the orbital pattern (131), the transmission window (135) may not always contain a satellite (130) to receive the message, as previously discussed. Including a timestamp of the detection time in the transmission eliminates the need to rely on transmission time as the timing indicator for the remote monitor.

In the example illustrated, a remotely placed AGM (110) on the surface (103) detects the passage of a pig (115) in a pipeline (101) carrying an attached transmitter. When the AGM (110) determines that a pig (115) has likely been detected, signal summary and other data is sent to a nearby satellite communications device (120) which initiates a series of repeated, identical message transmissions (133). At least one of these messages is received by satellite (130) and downlinked (136) to a ground station (140) and forwarded to the remote monitor (150) which utilizes the innovations described herein to reconstruct the data from the AGM detection.

FIG. 2 illustrated a data sample as seen by the AGM in the field. In this example, the detected signal (200) comprises a 22 Hz wave (201) with varying amplitude. Due to the sensitivity of the detectors, there is always some noise detected by the units which is ignored (210) if it remains below a specific threshold (207). The wave is a sinusoidal signal (201) which oscillates around a zero line (208). The AGM ignores the signal (201) unless it surpasses an upper (207A) or lower (207B) threshold.

Once the signal (201) crosses the threshold (207A or 207B), at 215, the AGM begins a recording sequence (217) where the wave is recorded. The timestamp (218) of the initial triggering sequence is recorded, to associate the data signal with a timeline (205) to determine known points in the signal (206). The primary data to be determined is the point (220) at which the pig crosses under the AGM, and the corresponding time (221) of that event.

Since the exact time of the event is not known and the amount of time for the event to occur is not known, the AGM determines an approach time period (231) characterized by a signal rise above a threshold and continuing to rise followed by a relatively quick fall in signal amplitude as the pig approaches and arrives under the AGM. The retreating period (233) is then determined to be a related time period immediately after the arrival characterized by a rise in signal amplitude to a maximum, followed by a slow decay as the pig continues along the pipeline away from the AGM.

FIG. 2A shows an enlarged portion of FIG. 2 illustrating the signal at the point in which data collection begins. The signal (201) is ignored (210) until a threshold (207A) is exceeded (215) at which the time is noted (217) and the signal recording begins.

FIG. 2B shows an enlarged portion of FIG. 2 illustrating the signal at the point in which the pig transverses the immediate detector area. The signal (201) decreases as it reaches a null point (220) where the amplitude tends toward the zero line (208) or dies away briefly.

Figure 3:
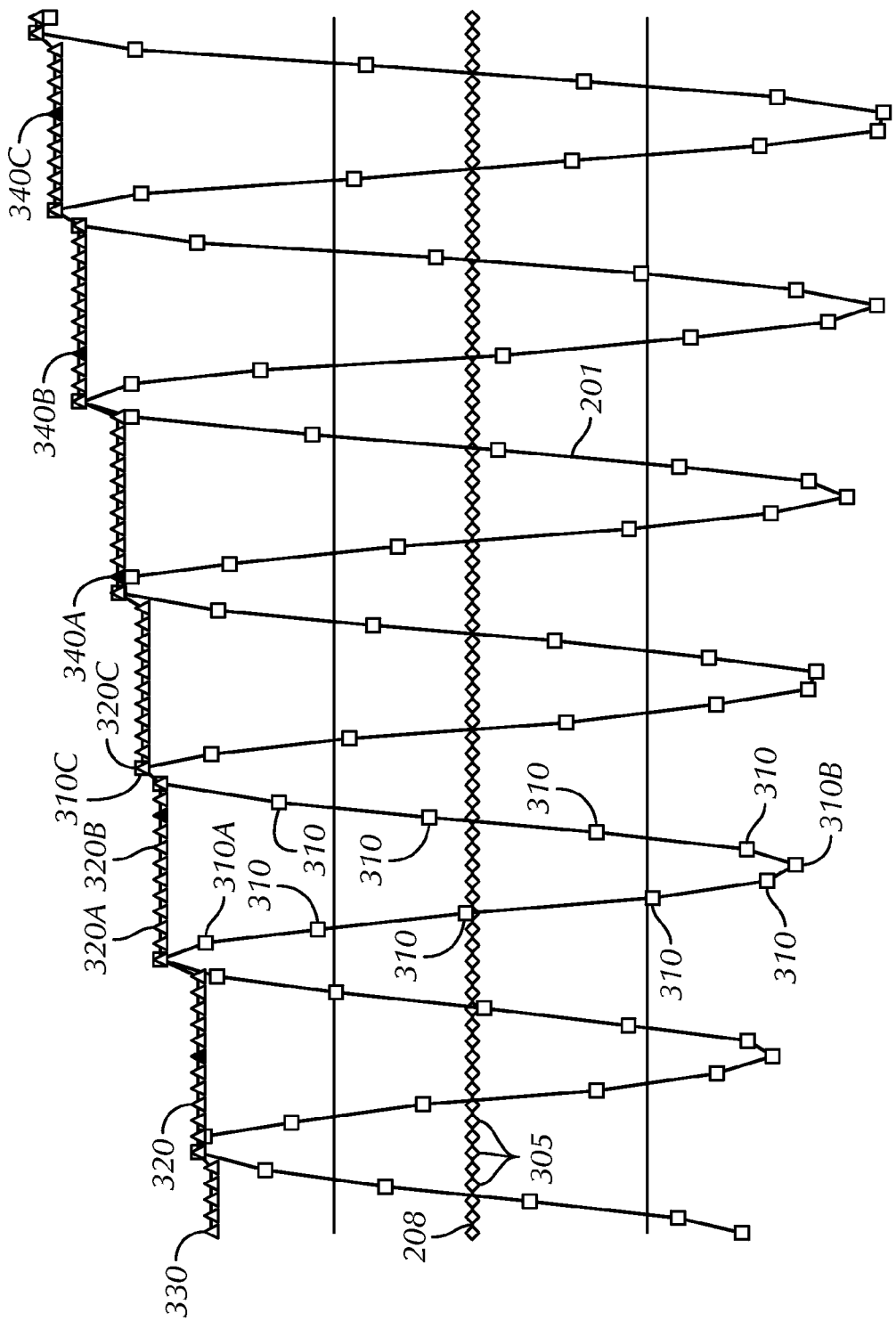
FIG. 3 illustrates the essential features of determining the data reduction in accordance with an exemplary embodiment of the invention.

FIG. 3 illustrates the essential features of determining the data reduction in an alternative method. The signal (201) is sampled at a predetermined interval indicated by the points (305) on the zero line (208) and values for the signal's amplitude (310) are determined. The sampled values (310) are then compared to determined peaks (310C) and an array (330) is established containing the value of the local peaks (320, 320A, 320B, 320C) to correspond to data points which are not peaks (310A, 310B). Finally a subset of these values (330) is selected (340A-C) as being representative of the shape of the wave.

Figure 4:
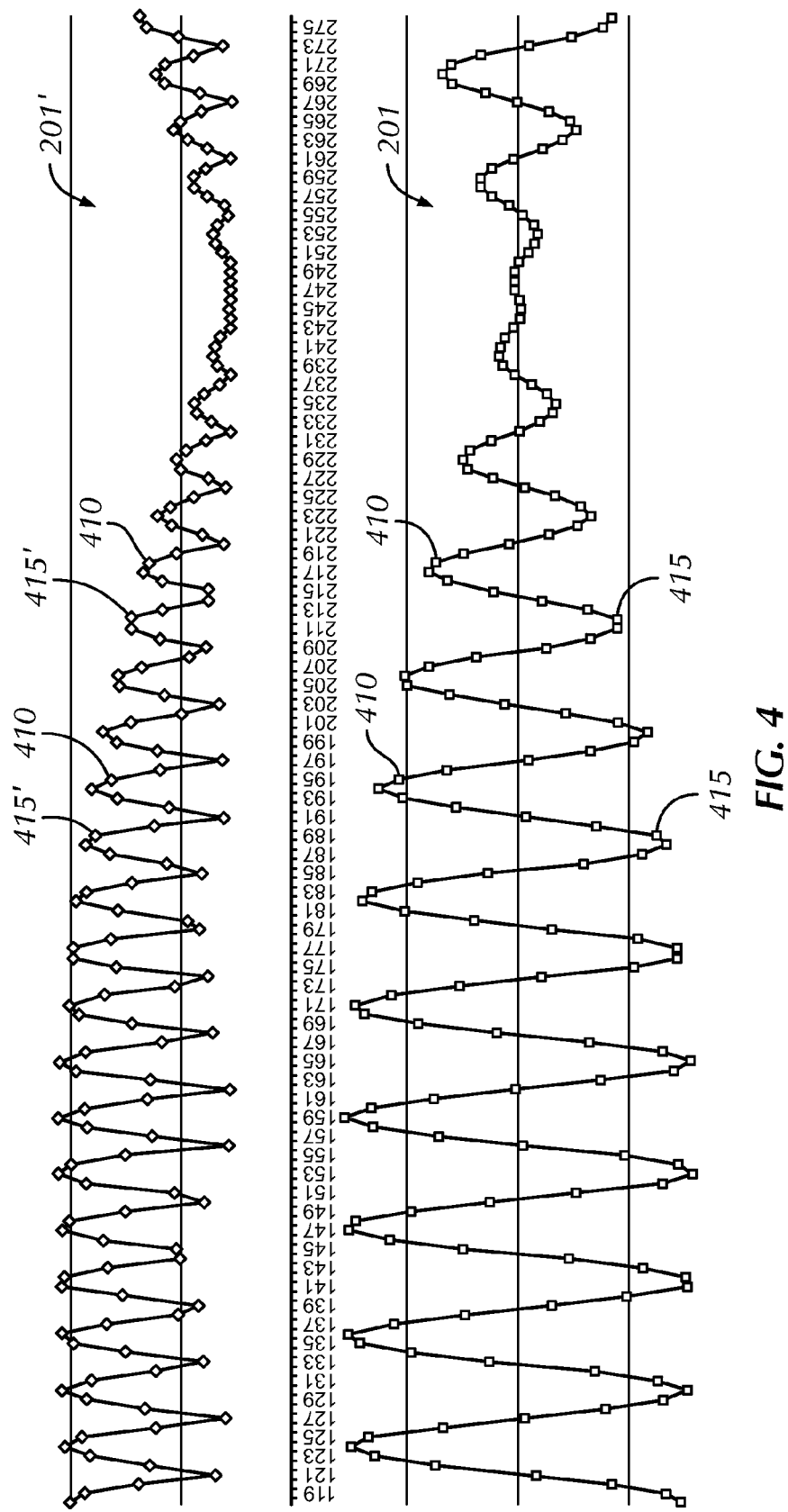
FIGS. 4 and 4A illustrate an alternative method of data reduction in accordance with an exemplary embodiment of the invention.
Figure 4A:
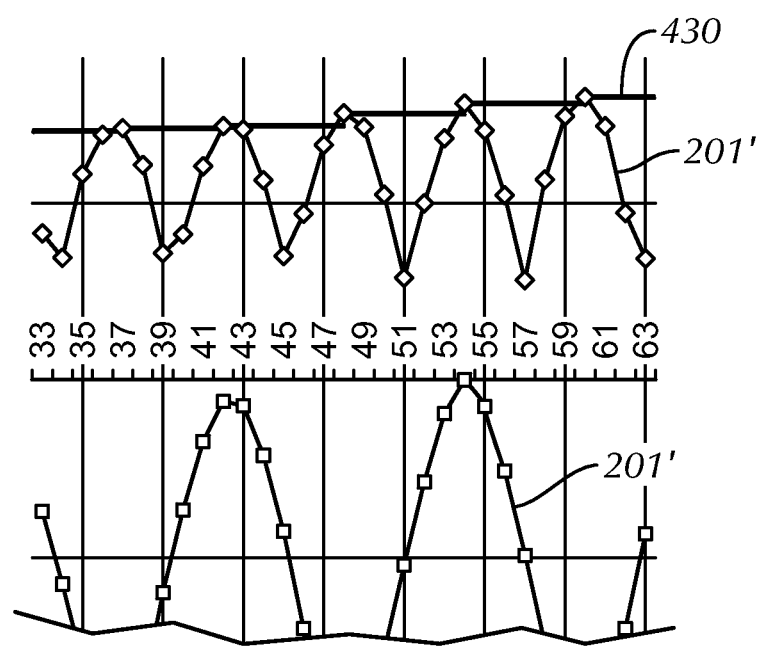

FIGS. 4 and 4A illustrate the preferred method of data reduction in accordance with an exemplary embodiment of the invention. This method is more complex than the method described above, but is preferred due to the increased resolution it provides. In this illustration, a signal (201) is rectified (201'). Original Peaks (410—bottom graph) remain unchanged (410—top graph), but the rectification flips valleys (415) into corresponding peaks (415'), resulting in double the peak count. At this point, a new peak curve (430) can be calculated for the new rectified curve (201') with double the resolution of the original data curve (201). The peak values are recorded (430) as shown in FIG. 4A.

FIG. 5 illustrates how the reduced data corresponds to and represents the original data. The data signal (201) was recorded beginning at a known point in time (217) designated by a timestamp which is transmitted as part of a data package. A minimum location is determined (550) near the actual null signal point (220). The plurality of data samples (340) represents the amplitude of the upper limits of the original signal (201) which is symmetrical about the zero line (208). Each successive pair (340', 340'') are utilized to estimate intermediate values of the signal as illustrated in FIGS. 6A & 6B.

FIGS. 6A and 6B illustrate a method of utilizing the reduced data to reconstruct the original data at a remote location in accordance with an exemplary embodiment of the invention. The amplitude of the signal (201, not indicated) above the zero line (608) is designated by a plurality of data points (340' and 340''). By knowing the frequency of the data, and the time of each sample, or the number of waves between each sample (X), an approximation of the original signal (201/601) can be reconstructed. By determining the curve (630) between the two known points (340' & 340''), the intermediate values (641A, 641B, 641C) can be determined, and the resulting curve (601, not indicated) can be completed.

Figure 7:
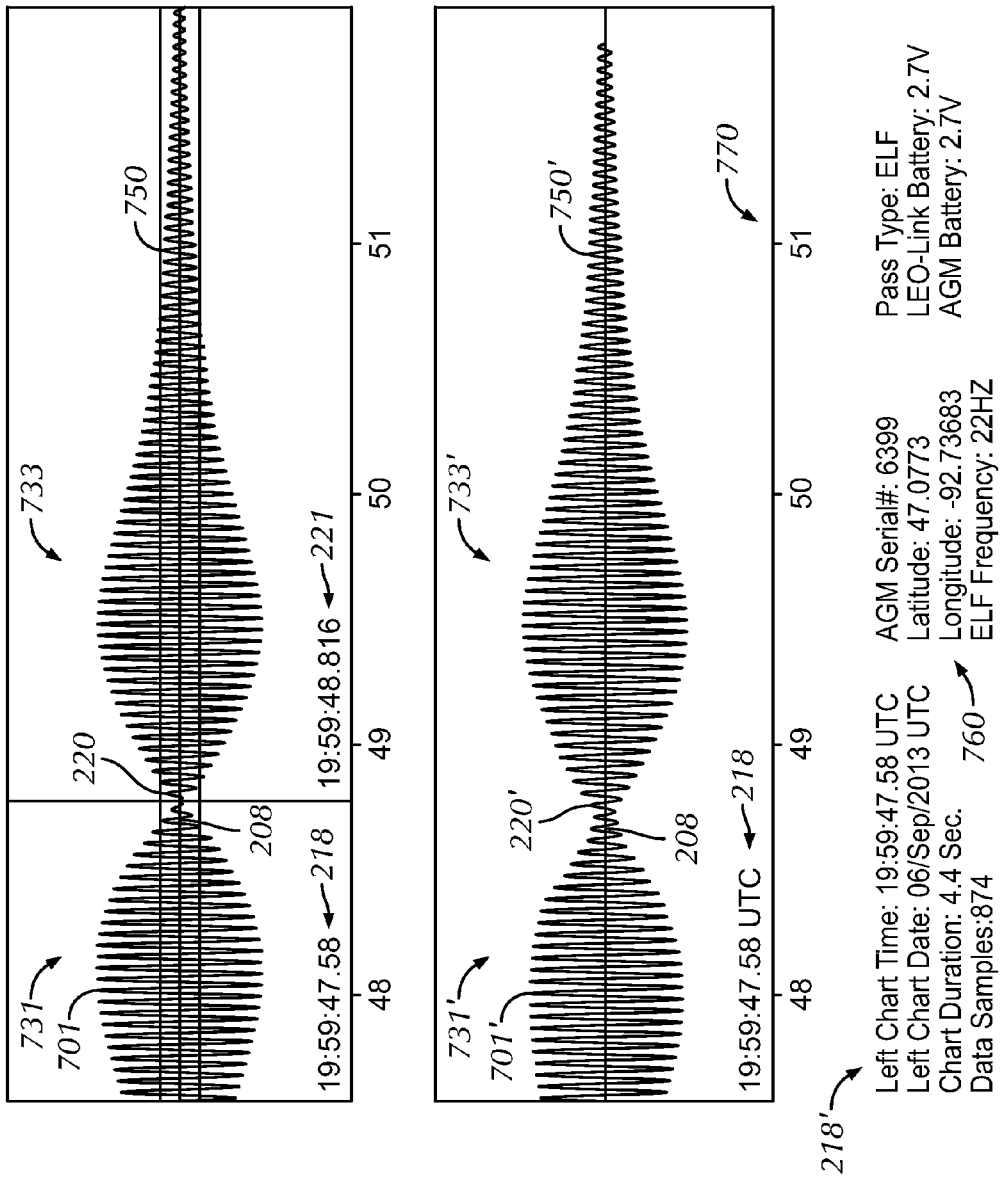
FIG. 7 shows a comparison between an exemplary detected signal, on the top half of the illustration, and a corresponding reconstruction report as it may be displayed to the receiver on the bottom half of the illustration.

FIG. 7 shows a comparison between an exemplary detected signal, on the top half of the illustration, and a corresponding reconstruction report as it may be displayed to the receiver on the bottom half of the illustration. FIG. 7 shows a typical "Good" pig pass for a 22 Hz Extremely Low Frequency (ELF) signal, as indicated by the labeling data (760) at the bottom screen representation. The raw signal (700) detected at the AGM is represented in the top diagram. The reconstructed data at the remote monitoring location is represented in the lower screen representation (701'). The data recording sequence starts at the left edge of the window as the signal exceeds a threshold. The event is time stamped by the Left Window Time (218), which is transmitted to the receiver and displays (218') with the labeling data (760) at the bottom of the screen. The characteristic rise and relatively quick fall of the approaching pig (731) to the crossing point (220) is followed by the relatively quick rise and slow fall of the retreating pig (733) until the signal decays down into noise (750). The crossing point (220) has a specific time (221) which is determinable relative to the signal start time (217) based on the data.

The data transmitted includes a series of data points and additional data (760) necessary to recreate the signal at the remote monitor. The displayed data (760) helps the operator confirm which data is being represented in the reconstructed data window (701'). By observing the approach signal (731') and the retreating signal (733' and 750'); the operator can classify the signal as representative of a Good pig pass, and identify the pass point (220'). The pass point's actual time can then be estimated based on the threshold crossing trigger point's (215, not indicated) time stamp (218) and the associated reconstructed timeline (770).

In the various embodiments in accordance with the present invention, embodiments are implemented as a method, system, and/or apparatus. As one example, exemplary embodiments are implemented as one or more computer software programs to implement the methods described herein. The software is implemented as one or more modules (also referred to as code subroutines, or "objects" in object-oriented programming). The location of the software will differ for the various alternative embodiments. The software programming code, for example, is accessed by a processor or processors of the computer or server from long-term storage media of some type, such as a CD-ROM drive or hard drive. The software programming code is embodied or stored on any of a variety of known media for use with a data processing system or in any memory device such as semi-conductor, magnetic and optical devices, including a disk, hard drive, CD-ROM, ROM, etc. The code is distributed on such media, or is distributed to users from the memory or storage of one computer system over a network of some type to other computer systems for use by users of such other systems. Alternatively, the programming code is embodied in the memory (such as memory of the handheld portable electronic device) and accessed by the processor using the bus. The techniques and methods for embodying software programming code in memory, on physical media, and/or distributing software code via networks are well known and will not be further discussed herein.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:
1. A method of reducing the data volume of a recorded data signal comprising:
    recording a segment of a detected signal;
    recording a time/date of at least one specific correlated point of the signal;
    determining a wave frequency of at least one component of the signal;
    sampling the amplitude of the waves at regular intervals;
    identifying peak amplitudes of the waves;
    identifying a subset of the peak amplitudes evenly distributed across the segment; and
    representing the segment of the detected signal by a reduced data volume comprising:
        the wave frequency,
        the time/date of a correlated signal point,
        a plurality of peak amplitude values, and
        the time difference between peak amplitude values;

transmitting the represented segment of the detected signal to a remote location;
receiving the represented segment at the remote location;
reconstructing the signal,
wherein reconstruction of the signal comprises:
for each discrete point of the reconstructed signal, determining the offset time between the discrete point and the time/date of the correlated signal point;
dividing the offset time by the time difference between peak amplitude values;
determining the signal amplitude at the discrete point by weighted average of the distance to the nearest neighbors in the plurality of amplitude values.

2. A method of reducing the data volume of a recorded data signal, as described in claim 1, wherein recording a segment of a detected signal comprises:
monitoring the detected signal; and
beginning recording of the signal once the amplitude of the signal exceeds a predefined threshold.

3. A method of reducing the data volume of a recorded data signal, as described in claim 2, wherein recording a segment of a detected signal further comprises:
ending the recording of the signal once the amplitude of the signal fails to exceed a predefined threshold for a predetermined amount of time.

4. A method of reducing the data volume of a recorded data signal, as described in claim 1, wherein a wave frequency of the signal is predetermined by a band pass filter on the detector.

5. A method of reducing the data volume of a recorded data signal, as described in claim 1, wherein the interval for sampling the amplitude of the waves is determined by the wave frequency.

6. A method of reducing the data volume of a recorded data signal, as described in claim 1, wherein the size of the subset of the peak amplitudes evenly distributed across the segment is determined by the desired reduced data volume.

7. A method of reducing the data volume of a recorded data signal, as described in claim 1, wherein the size of the subset of the peak amplitudes evenly distributed across the segment is determined by the desired resolution of a signal to be recreated from the reduced data volume.

8. A method of reducing the data volume of a recorded data signal, as described in claim 1, wherein the correlated point of the signal is the first point at which the detected signal exceeds a predetermined threshold value.

9. A method of reducing the data volume of a recorded data signal, as described in claim 1, wherein the correlated point of the signal is the first point at which the detected signal is recorded.

10. A method of reducing the data volume of a recorded data signal, as described in claim 1, wherein the plurality of peak amplitude values is further reduced to characteristics of the derivatives of one or more curves represented by the discrete values.

11. A method of reducing the data volume of a recorded data signal, as described in claim 1, wherein the segment of a detected signal is determined by manual selection by a user monitoring the recorded data signal.

12. A method of reducing the data volume of a recorded data signal, as described in claim 1, wherein the wave frequency of at least one component of the signal is determined to be zero because there is no carrier wave component of the recorded data signal.

13. A method of reconstructing a signal from a reduced data volume comprising:
recording a segment of a detected signal;
recording a time/date of at least one specific correlated point of the signal;
determining a wave frequency of at least one component of the signal;
sampling the amplitude of the waves at regular intervals;
identifying peak amplitudes of the waves;
identifying a subset of the peak amplitudes evenly distributed across the segment;
wherein the reduced data volume comprises:
the wave frequency,
the time/date of a correlated signal point,
a plurality of peak amplitude values, and
the time difference between peak amplitude values;
wherein reconstruction of the signal comprises:
for each discrete point of the reconstructed signal, determining the offset time between the discrete point and the time/date of the correlated signal point;
dividing the offset time by the time difference between peak amplitude values;
determining the signal amplitude at the discrete point by weighted average of the distance to the nearest neighbors in the plurality of amplitude values.

14. A method of reconstructing a signal from a reduced data volume, as described in claim 13, wherein reconstruction of the signal further comprises:
imposing a carrier wave of the wave frequency with corresponding amplitude at each discrete point of the reconstructed signal.

15. A method of reconstructing a signal from a reduced data volume, as described in claim 13, wherein reconstruction of the signal further comprises:
imposing a plurality of times upon a plurality of discrete point of the reconstructed signal.

16. A method of reconstructing a signal from a reduced data volume, as described in claim 13, wherein the reconstructed signal is displayed on a monitoring device.

17. A method of reconstructing a signal from a reduced data volume, as described in claim 13, wherein the reconstructed signal is interpreted by a computing device.

18. A method of remotely reproducing a data signal comprising:
recording a segment of a detected signal at a first location;
recording a time/date of at least one specific correlated point of the signal;
determining a wave frequency of at least one component of the signal;
sampling the amplitude of the waves at regular intervals;
identifying peak amplitudes of the waves;
identifying a subset of the peak amplitudes evenly distributed across the segment;
representing the segment of the detected signal by a reduced data volume comprising:
the wave frequency,
the time/date of a correlated signal point,
a plurality of peak amplitude values, and
the time difference between peak amplitude values;
transmitting the represented segment of the detected signal to a remote location;
receiving the represented segment at the remote location;
reconstructing the signal,
wherein reconstruction of the signal comprises:
for each discrete point of the reconstructed signal, determining the offset time between the discrete point and the time/date of the correlated signal point;

dividing the offset time by the time difference between peak amplitude values;

determining the signal amplitude at the discrete point by weighted average of the distance to the nearest neighbors in the plurality of amplitude values.

* * * * *